United States Patent [19]

Fancher

[11] 4,115,558
[45] Sep. 19, 1978

[54] HYDRAZONE DITHIOPHOSPHATES AND PHOSPHONATES AND USE THEREOF AS INSECTICIDES

[75] Inventor: Llewellyn W. Fancher, Orinda, Calif.

[73] Assignee: Stauffer Chemical Company, Westport, Conn.

[21] Appl. No.: 843,999

[22] Filed: Oct. 20, 1977

[51] Int. Cl.² .................. A01N 9/36; C07F 9/40; C07F 9/165
[52] U.S. Cl. ..................... 424/205; 260/923; 260/968
[58] Field of Search .................. 260/923; 424/205

[56] References Cited

U.S. PATENT DOCUMENTS

| | | | |
|---|---|---|---|
| 2,901,481 | 8/1959 | Fusco et al. | 260/928 |
| 3,094,550 | 6/1963 | Schör et al. | 260/928 |
| 3,317,426 | 5/1967 | Lowe | 260/928 |
| 3,517,088 | 6/1970 | Gutman et al. | 260/928 |
| 3,518,327 | 6/1970 | Fearing | 260/923 |
| 3,537,988 | 11/1970 | Lowe | 260/928 |
| 3,678,165 | 7/1972 | Fearing | 424/211 |

*Primary Examiner*—Anton H. Sutto
*Attorney, Agent, or Firm*—Joel G. Ackerman

[57] ABSTRACT

Novel insecticidal compounds have the general structural formula

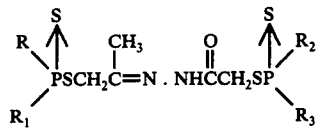

in which each of R and $R_2$ is an alkyl or alkoxy group and each $R_1$ and $R_3$ is an alkoxy group.

21 Claims, No Drawings

HYDRAZONE DITHIOPHOSPHATES AND PHOSPHONATES AND USE THEREOF AS INSECTICIDES

SUMMARY OF THE INVENTION

This invention relates to novel hydrazone dithiophosphates and dithiophosphonates and to their use as insecticides.

The novel compounds of this invention have the general structural formula

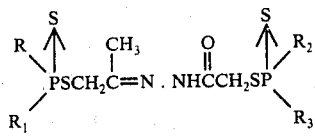

in which each of R and $R_2$ is an alkyl or alkoxy group and each of $R_1$ and $R_3$ is an alkoxy group.

By "alkyl" is meant a straight- or branched-chain saturated hydrocarbon group containing 1 to 4 carbon atoms, i.e., ethyl, methyl, n-propyl, isopropyl, butyl, isobutyl, sec-butyl, and tert.-butyl. Particularly preferred alkyl groups are methyl and ethyl.

By "alkoxy" is meant a straight- or branched-chain saturated hydrocarbonoxy group containing 1 to 4 carbon atoms. Examples of groups conforming to this description are methoxy, ethoxy, n-propoxy, isopropoxy, butoxy, isobutoxy, sec-butoxy, and tert.-butoxy. Particularly preferred alkoxy groups are methoxy and ethoxy.

The novel compounds of this invention are insecticidal, that is, they kill, substantially injure or otherwise inhibit the growth of insects. The compounds can be applied in any conventional manner to the habitat of insects, the feedstuffs of insects or the insects themselves. The amount of the particular compound required to produce the desired degree of control of insects will vary depending on the insects to be controlled and the method of application. One skilled in the art, with the teaching of this specification before him, will be able, without undue experimentation to determine the insecticidally effective amount for the desired effect. The compounds are particularly effective against aphids.

DETAILED DESCRIPTION OF THE INVENTION

The compounds of this invention can be prepared by reacting a propanone dithiophosphate or phosphonate with a dithiophosphoro- or phosphono-acetyl hydrazide.

A. Preparation of the Intermediates

The intermediate propanone dithiophosphates and phosphonates can be prepared by reacting chloroacetone with the appropriate dithiophosphoric or phosphonic acid.

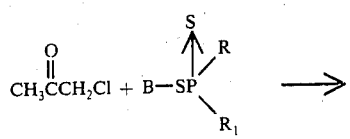

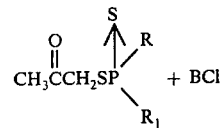

wherein R and $R_1$ are defined as above, and B is a base such as sodium, potassium, ammonia, triethylamine, and the like. Preferably a solvent, such as dimethylformamide, or other inert solvent, such as ketones or dimethyl sulfoxide, is utilized in this reaction. Reaction time is not critical and can vary from a few hours to overnight. The product is isolated by dilution with water and extraction with a suitable solvent, such as benzene.

The intermediate dithiophosphoro- and phosphonoacetyl hydrazides can be prepared by reacting an appropriate dithiophosphoro- or phosphono-acetate with hydrazine hydrate.

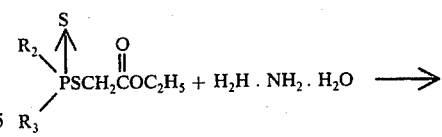

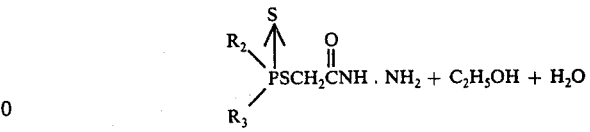

wherein $R_2$ and $R_3$ are as defined above. The reaction preferably is conducted in the presence of a solvent. Ethanol is a preferred solvent, but other alcohols can also be used. Reaction time can vary from a few hours to overnight. The solution should be refluxed to insure completion of the reaction. The product may be isolated by vacuum evaporation of the ethanol and water from the reaction mixture following completion of the reaction.

B. Preparation of Final Compounds

The novel hydrazone dithiophosphonates and phosphonates of this invention are prepared by reacting a propanone dithiophosphate or phosphonate with a dithiophosphoro or phosphono acetyl hydrazide.

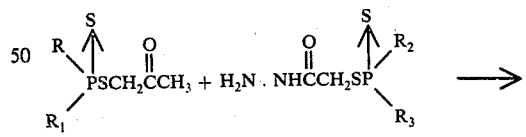

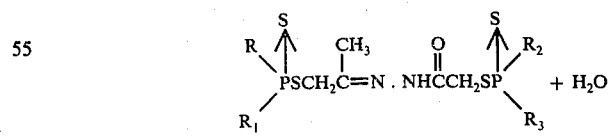

This reaction proceeds by azeotropic distillation in which a solvent that is not miscible in water is refluxed while water is continuously removed as a separate layer. Solvents which will azeotropically remove water, such as benzene, are used in this step. The reaction mixture is then cooled and mixed with a drying agent such as anhydrous magnesium sulfate to remove additional water. It is then filtered and rinsed, and finally the solvent is evaporated under vacuum.

The following examples illustrate the preparation of typical compounds of this invention and demonstrate their utility as insecticides.

EXAMPLE 1

O,O-DIETHYLPHOSPHORODITHIOYLPROPANONE-O,O DIETHYLPHOSPHORODITHIOACETYL-HYDRAZONE

A solution of 51.5 grams (0.23 mole) of the potassium salt of O,O-diethyldithiophosphoric acid, dissolved in 75 milliliters of dimethylformamide was prepared. To this solution was added 18.5 grams (0.2 mole) of monochloroacetone, with the temperature maintained by cooling at below 40° C. The mixture was stirred at ambient temperature for 4 hours. The mixture was then diluted with 100 milliliters of benzene, washed with dilute sodium chloride solution, dried over anhydrous magnesium sulfate, evaporated under vacuum and air stripped on a steam bath. A yield of 47.7 grams of a liquid product having a refractive index, $n_D^{30}$ of 1.5143, was obtained. The structure of the product, O,O-diethylphosphorodithioyl propanone, was confirmed by IR and NMR.

A solution of 48.0 grams (0.17 mole) of ethyl O,O-diethylphosphorodithioacetate dissolved in 70 milliliters of ethanol was prepared. To this solution was added 8.80 grams (0.176 mole) of hydrazine hydrate, with the temperature maintained by cooling below 10° C. The mixture was stirred at ambient temperature for 3 hours, allowed to stand overnight, and then refluxed for 2 hours on a steam bath. The reaction mixture was then evaporated and stripped under vacuum, producing 46.20 grams of a white semi-solid, soluble in acetone. The structure of the product, O,O-diethylphoshorodithioyl-S-acetyl hydrazide, was confirmed by NMR analysis.

To 100 milliliters of benzene was added 3.63 grams (0.015 mole) of O,O-diethylphosphorodithioyl propanone prepared in the first paragraph above, and 3.87 grams (0.015 mole) of O,O-diethylphosphorodithioyl-S-acetyl hydrazide prepared in the second paragraph above. This solution was refluxed for 2 hours with stirring. The water was continuously removed azeotropically. The reaction mixture was then cooled, dried with anhydrous magnesium sulfate, filtered and evaporated and stripped under high vacuum. A yield of 6.45 grams of a thick yellow liquid having a refractive index, $n_D^{30}$ of 1.5470, was obtained. The structure of the product, O,O-diethylphosphorodithioyl-propanone-O,O-diethylphosphorodithioyl-acetylhydrazone, was confirmed by NMR.

EXAMPLE 2

ETHYL O-ETHYLPHOSPHONODITHIOYLPROPANONE-O,O-DIETHYLPHOSPHORODITHIOLACETYL-HYDRAZONE

A solution of 18.5 grams (0.2 mole) of chloroacetone, 39.1 grams (0.23 mole) of ethyl O-ethyldithiophosphonic acid dissolved in 50 milliliters of dimethylformamide was prepared with cooling to maintain the temperature below 15° C. Then 23.2 grams (0.23 mole) of triethylamine was added dropwise over a period of 10 minutes, with temperature kept below 20° C. The mixture was stirred at ambient temperature for 3 hours and left standing overnight. It was then diluted with benzene, washed with dilute sodium chloride solution, dried over anhydrous magnesium sulfate, evaporated under vacuum and air stripped on a steam bath. A yield of 44.8 grams of a light brown liquid having a refractive index, $n_D^{30}$ of 1.5340, was obtained. This product is ethyl O-ethylphosphonodithioyl propanone.

A solution of 3.39 grams (0.015 mole) of this compound and 3.87 grams (0.015 mole) of O,O-diethylphosphorodithioyl-S-acetylhydrazide (prepared as in Example 1) in 100 milliliters benzene was prepared. This solution was refluxed for 2 hours with stirring. The water was continuously removed azeotropically. The reaction mixture was then cooled, dried with anhydrous magnesium sulfate, filtered and evaporated and stripped under high vacuum. A yield of 6.59 grams of a thick orange liquid having a refractive index, $n_D^{30}$ of 1.5582 was obtained. The structure of the product, ethyl O-ethylphosphonodithioylpropanone-O,O-diethylphosphorodithioyl acetyl hydrazone, was confirmed by NMR.

The compounds listed in the following Table I include the compounds prepared above and are illustrative of the compounds encompassed by the present invention. These compounds can be prepared in an analogous manner to those whose preparation is described in detail above. Appropriate starting materials will be readily apparent to one skilled in the art. Compound numbers have been assigned to these compounds and are then used throughout the remainder of the specification.

TABLE I $$\underset{R_1}{\overset{R}{\diagdown}}P\overset{S}{\overset{\|}{\phantom{P}}}SCH_2\underset{CH_3}{\overset{\phantom{|}}{\overset{|}{C}}}=N \cdot NHCCH_2SP\overset{S}{\overset{\|}{\phantom{P}}}\underset{R_3}{\overset{R_2}{\diagup}}$$

| Compound Number | R | $R_1$ | $R_2$ | $R_3$ | $n_D^{30}$ |
|---|---|---|---|---|---|
| 1 | $OC_2H_5$ | $OC_2H_5$ | $OC_2H_5$ | $OC_2H_5$ | 1.5470 |
| 2 | $C_2H_5$ | $OC_2H_5$ | $OC_2H_5$ | $OC_2H_5$ | 1.5582 |
| 3 | $OCH_3$ | $OCH_3$ | $OC_2H_5$ | $OC_2H_5$ | 1.5566 |
| 4 | $OC_2H_5$ | $OC_2H_5$ | $C_2H_5$ | $OC_2H_5$ | 1.5607 |
| 5 | $C_2H_5$ | $OC_2H_5$ | $C_2H_5$ | $OC_2H_5$ | 1.5742 |
| 6 | $OCH_3$ | $OCH_3$ | $C_2H_5$ | $OC_2H_5$ | 1.5771 |

INSECTICIDE EVALUATION PROCEDURES

Contact Residue Assay on the Housefly (HF), [*Musca domestica* (L.)]

Test compounds are diluted in acetone and aliquots are pipetted on the bottom of 55 × 15 milliliter aluminum dishes. To insure even spreading of the chemical on the bottom of the dishes, one milliliter of acetone containing 0.02% peanut oil is also added to each dish. After all solvents have evaporated the dishes are placed in circular cardboard cages containing 25 female houseflies. The cages are covered on the bottom with cellophane and the top with tulle netting. Each cage contains a sugar-water saturated cotton plug for maintenance of the flies. Mortality is recorded after 48 hours. Test levels range from 100 micrograms per 25 female ($\mu$g/25 ♀) houseflies down to that at which approximately 50% mortality occurs.

Direct Spray Assay on German Cockroach (GR), [*Blattella germanica* (Linne)]

Test compounds are diluted in a 50—50 acetone-water solution. Two cubic centimeters of the solutions are sprayed through a DeVilbiss type EGA hand spray gun into circular cardboard cages containing ten one-month-old German cockroach nymphs. The test cages are covered on the bottom with cellophane and the top with tulle netting. Percent mortality is recorded 7 days later. Test concentrations range from 0.1% down to that at which approximately 50% mortality occurs.

Direct Spray Assay on Lygus Bug (LB), [*Lygus hesperus* (Knight)]

Test compounds are in a 50—50 acetone-water solution. Two cubic centimeters of the solution is sprayed through a DeVilbiss type EGA hand spray gun into circular cardboard cages containing one string bean pod and ten adult lygus bugs. The test cages are covered on the bottom with cellophane and the top with tulle netting. Percent mortality is recorded 48 hours later. Test concentrations range from 0.05% down to that at which approximately 50% mortality occurs.

Direct Spray Assay on Black Bean Aphid (BA), [*Aphis fabae* (Scop.)]

Nasturtium plants (*Tropaeolum sp.*), approximately 5 centimeters tall, are transplanted into sandy loam soil in 3 inch clay pots and infested with 25-50 black bean aphids of mixed ages. Twenty-four hours later they are sprayed, to the point of runoff, with 50—50 acetone-water solutions of the test chemicals. Treated plants are held in the greenhouse and mortality is recorded after 7 days. Test concentrations range from 0.05% down to that at which 50% mortality occurs.

Systemic Assay on Black Bean Aphid (BA syst), [*Aphis favae* (Scop.)]

Test chemicals are diluted in acetone and aliquots are thoroughly mixed into 500 grams of dry, sandy loam soil. The treated soil is placed in a pint ice cream carton and a nasturtium plant (*Tropaeolum sp.*) approximately 5 centimeters tall is transplanted into each carton. The plants are then infested with approximately 25 black bean aphids of mixed ages and placed in the greenhouse. Seven days later mortality is recorded. Test concentrations range from 10 parts per million down to that at which approximately 50% mortality occurs.

Direct Spray Assay on Green Peach Aphid (GPA), [*Myzus persicae* (Sulzer)]

Radish plants (*Rhaphanus sativus*), approximately 2 centimeters tall, are transplanted into sandy loam soil in 3 inch clay pots and infested with 25-50 green peach aphids of mixed ages. Twenty-four hours later they are sprayed, to the point of runoff, with 50—50 acetone-water solutions of the test chemicals. Treated plants are held in the greenhouse and mortality is recorded after 48 hours. Test concentrations range from 0.05% down to that at which 50% mortality occurs.

Leaf Dip Assay on Third Instar Salt-Marsh Caterpillar Larvae (SMC), [*Estigmene acrea* (Drury)]

Test compounds are diluted in a 50—50 acetone-water solution. Sections of curly dock (*Rumex crispus*) leaves, approximately 1 × 1.5 inches, are immersed in the test solutions for 2-3 seconds and placed on a wire screen to dry. The dried leaves are placed in petri dishes containing a moistened piece of filter paper and infested with five third-instar salt-marsh larvae. Mortality of the larvae is recorded after 48 hours, and a piece of synthetic media is added to dishes containing survivors. These are then held for 5 additional days to observe for any delayed effects of the test chemicals. Test concentrations range from 0.05% down to that at which approximately 50% mortality occurs.

Leaf Dip Assay on Tobacco Budworm Larvae (TBW), [*Heliothis virescens* (F.)]

Test compounds are diluted in a 50—50 acetone-water solution. Sections of Romaine lettuce (*Latuca sativa*) leaves, approximately 1 × 1.5 inches, are immersed in the test solutions for 2-3 seconds and placed on a wire screen to dry. The dried leaves are placed in petri dishes containing a moistened piece of filter paper and infested with five second-instar tobacco budworm larvae. Mortality of the larvae is recorded 48 hours later, and a piece of synthetic media is added to dishes containing survivors. These are then held for 5 additional days to observe for any delayed effects of the test chemicals. Test concentrations range from 0.1% to that at which approximately 50% mortality occurs.

Leaf Dip Assay on Cabbage Looper Larvae (CL), [*Trichloplusia ni* (Hübner)]

Test compounds are diluted in a 50—50 acetone-water solution. Cotyledons of hyzini squash (*Calabacita abobrinha*), approximately 1 × 1.5 inches, are immersed in the test solutions for 2-3 seconds and placed on a wire screen to dry. The dried leaves are placed in petri dishes containing a moistened piece of filter paper and infested with five second-instar cabbage looper larvae. Mortality of the larvae is recorded 48 hours later, and a piece of synthetic media is added to dishes containing survivors. These are then held for 5 additional days to observe for any delayed effects of the test chemicals. Test concentrations range from 0.1% to that at which approximately 50% mortality occurs.

Insecticidal Assay on Southern House Mosquito Larvae (MOS), [*Culex pipiens quinquefasciatus* (Say)]

Insecticidal activity is determined using third-instar larvae of the mosquito (*Culex pipiens quinquefasciatus*). Ten larvae are placed in a 6 ounce, number 67 Dixie wax paper cup containing 100 ml of an aqueous solution of the test chemical. The treated larvae are stored at 70° F, and 48 hours later the mortality is recorded. Test concentrations range from 0.5 ppm down to that at which approximately 50% mortality occurs.

Plant Dip Assay on Two-Spotted Mite (SM-1), [*Tetranychus urticae* (Koch)]

Pinto bean plants (*Phaseolus vulgaris*) approximately 10 centimeters tall, are transplanted into sandy loam soil in 3 inch clay pots and thoroughly infested with two-spotted mites of mixed ages and sexes. Twenty-four hours later the infested plants are inverted and dipped for 2-3 seconds in 50—50 acetone-water solutions of the test chemicals. Treated plants are held in the greenhouse, and 7 days later mortality is determined for both the adult mites and the nymphs hatching from eggs which were on the plants at the time of treatment. Test concentrations range from 0.05% down to that at which 50% mortality occurs.

Ovicide Test on Two-Spotted Spider Mite (SM-2),
[*Tetranychus urticae* (Koch)]

Mite infested pinto bean (*Phaseolus vulgaris*) plants are dipped in a 0.05% (50/50 acetone-water) solution of Phosdrin ® (Phosdrin kills most of the post-embryonic forms but is not effective against the eggs at 0.05%). After the leaves have dried, they are treated with the test compound at the desired concentrations. One week later, the plants are examined for the presence of immature mites.

Systemic Assay on Two-Spotted Mites (SM-3),
[*Tetranychus urticae* (Koch)]

Test chemicals are dissolved in acetone and aliquots are diluted in 200 cubic centimeters of water in glass bottles. Two pinto bean plants (*Phaselous vulgaris*), with expanded primary leaves are supported in each bottle by cotton plugs, so that their roots and stems are immersed in the treated water. The plants are then infested with 75-100 two-spotted mites of various ages and sexes. One week later the mortality of the adult mites and nymphs is recorded. Test concentrations range from 10 parts per million down to that at which 50% mortality occurs.

The primary screening level for each of the above tests was chosen for purposes of convenience only, and is not intended to represent the highest level at which a test for insecticidal activity can be practically conducted.

Each compound was initially tested at the primary screening level for the particular insect test. Those compounds effecting more than 50 percent mortality at this level were then tested at progressively lower doses, until the level was reached at which there was approximately 50 percent mortality. For those compounds which showed approximately 50 percent mortality at the primary screening level, the primary screening level itself is listed as the $LD_{50}$ (50 percent lethal dose) value in Table II. Values preceded by a ">" (greater than) sign indicate that a dose higher than the primary screening level must be used to produce a 50 percent mortality. Since no tests were run at concentrations higher than the primary screening level, it cannot be concluded definitely what the activity of these compounds would be at higher concentrations. Values proceded by a "<" (less than) sign indicate that the true $LD_{50}$ level is somewhat lower than that indicated. However, no tests were run at concentrations below this level. For all other results, $LD_{50}$ is equal to the value indicated.

TABLE II

| Compound Number | HF μg/25 ♀ | GR (%) | LB (%) | BA (%) | BA syst (ppm) | GPA (%) | SMC (%) | TBW (%) | CL (%) | MOS (ppm) | SM-1 (%) | SM-2 (%) | SM-3 (%) |
|---|---|---|---|---|---|---|---|---|---|---|---|---|---|
| 1 | 75 | >.1 | >.05 | .03 | >10 | >.05 | >.05 | >.1 | >.1 | 1 | .05 | <.05 | >10 |
| 2 | 32 | >.1 | >.05 | .005 | >10 | .005 | >.05 | >.1 | >.1 | .5 | <.05 | <.05 | >10 |
| 3 | 55 | >.1 | >.05 | .01 | >10 | .05 | >.05 | >.1 | >.1 | .8 | .05 | .05 | >10 |
| 4 | 30 | >.1 | >.05 | .003 | >10 | .005 | >.05 | >.1 | >.1 | .1 | <.05 | <.05 | >10 |
| 5 | 28 | >.1 | >.05 | .002 | >10 | .005 | >.05 | >.1 | >.1 | .1 | <.05 | <.05 | >10 |
| 6 | 30 | >.1 | >.05 | .003 | 10 | .005 | >.05 | .1 | .1 | .2 | <.05 | <.05 | >10 |

Insecticidal Effectiveness - Approximate $LD_{50}$ Values

HF - Housefly
GR - German cockroach
LB - Lygus bug
BA - Black bean aphid (direct spray)
BA syst - Black bean aphis (systemic)
GPA - Green peach aphid
SMC - Salt-marsh caterpillar
TBW - Tobacco budworm
CL - Cabbage Looper
MOS - Mosquito
SM - Two-spotted mite
-1 - plant dip
-2 - ovicides
-3 - systemic
> - "greater than" indicates $LD_{50}$ level is higher than the primary screening level
< - "less than" indicates $LD_{50}$ level is lower than the value indicated The insecticidal compounds of this invention are generally applied to the locus where control of insects is desired in the form of formulations containing the compound and an inert carrier. Such formulations generally contain up to 80% by weight of the active ingredient. Insecticidal formulations generally take the form of dusts, wettable powders, granules, solutions, emulsifiable concentrates, or the like.

Dusts are free-flowing powder compositions containing the insecticidal compound impregnated on a particulate carrier. The particle size of the carrier is usually in the range of from about 30 to 50 microns. Examples of suitable carriers are talc, bentonite, diatomaceous earth, and pyrophyllite. Anticaking and antistatic agents can be added if desired.

Wettable powders are finely divided compositions comprising a particulate carrier impregnated with the insecticidal compound and additionally containing one or more surface active agents. The surface active agent promotes rapid dispersion of the powder in aqueous medium to form stable, sprayable suspensions. A wide variety of surface active agents can be used, for example, long chain fatty alcohols and alkali metal salts of the sulfated fatty alcohols, salts of sulfonic acid, esters of long chain fatty acids and polyhydric alcohols and the like. A list of surface active agents suitable for use in agriculture formulations can be found in *Pesticide Formulations* by Wade Van Valkenburg, Marcel Dekker, Inc., N.Y. 1973 at pages 79-84.

Granules comprise the insecticidal compound impregnated on a particular inert carrier having a particle size of 1 to 2 millimeters in diameter. The granules can be made by spraying a solution of the active ingredient in a volatile solvent onto the granular carrier. Suitable carriers in preparation of granules include clay, vermiculite, sawdust, granular carbon and the like.

The insecticidal compounds can also be applied to the soil in the form of a solution in a suitable solvent. Solvents frequently used in pesticidal formulations include kerosene, fuel oil, xylene, petroleum fractions with boiling ranges above xylene, and aromatic petroleum fractions rich in methylated naphthalenes.

Emulsifiable concentrates consist of an oil solution of the insecticidal compound along with an emulsifying agent. Prior to use the concentrate is diluted with water to form a suspended emulsion of oil droplets. The emulsifiers used are usually a mixture of anionic and nonionic surfactants. Other additives such as spreading agents and stickers can be included in the emulsifiable concentrate if desired.

The compositions are applied to the locus where control of insects is desired in an insecticidally effective amount. In a preferred method of application, the insecticide is applied as a solution of suspension from conventional spray apparatus. The solutions or suspensions contain about 0.01 to about 5.0%, preferably about 0.1 to about 2.0% by weight of the insecticide.

What is claimed is:

1. A method of controlling insects comprising applying to said insects or the habitat or feedstuff of said insects an insecticidally effective amount of a compound having the general structural formula $$\begin{array}{c} R\diagdown \overset{S}{\underset{\diagup}{\uparrow}} \\ R_1 \end{array} PSCH_2\overset{CH_3}{\underset{|}{C}}=N \cdot NH\overset{O}{\underset{\|}{C}}CH_2SP \begin{array}{c} \diagup R_2 \\ \diagdown R_3 \end{array}$$

in which each of R and $R_2$ is an alkyl or alkoxy group and each of $R_1$ and $R_3$ is an alkoxy group.

2. A method according to claim 1 in which R is $OC_2H_5$, $R_1$ is $OC_2H_5$, $R_2$ is $OC_2H_5$ and $R_3$ is $OC_2H_5$.

3. A method according to claim 1 in which R is $C_2H_5$, $R_1$ is $OC_2H_5$, $R_2$ is $OC_2H_5$ and $R_3$ is $OC_2H_5$.

4. A method according to claim 1 in which R is $OCH_3$, $R_1$ is $OCH_3$, $R_2$ is $OC_2H_5$ and $R_3$ is $OC_2H_5$.

5. A method according to claim 1 in which R is $OC_2H_5$, $R_1$ is $OC_2H_5$, $R_2$ is $C_2H_5$ and $R_3$ is $OC_2H_5$.

6. A method according to claim 1 in which R is $C_2H_5$, $R_1$ is $OC_2H_5$, $R_2$ is $C_2H_5$ and $R_3$ is $OC_2H_5$.

7. A method according to claim 1 in which R is $OCH_3$, $R_1$ is $OCH_3$, $R_2$ is $C_2H_5$ and $R_3$ is $OC_2H_5$.

8. An insecticidally effective composition of matter comprising (a) an insecticidally effective amount of a compound having the general structural formula $$\begin{array}{c} R\diagdown \overset{S}{\underset{\diagup}{\uparrow}} \\ R_1 \end{array} PSCH_2\overset{CH_3}{\underset{|}{C}}=N \cdot NH\overset{O}{\underset{\|}{C}}CH_2SP \begin{array}{c} \diagup R_2 \\ \diagdown R_3 \end{array}$$

in which each of R and $R_2$ is an alkyl or alkoxy group and each of $R_1$ and $R_3$ is an alkoxy group, and;

(b) an inert carrier therefor.

9. A composition according to claim 8 in which R is $OC_2H_5$, $R_1$ is $OC_2H_5$, $R_2$ is $OC_2H_5$ and $R_3$ is $OC_2H_5$.

10. A composition according to claim 8 in which R is $C_2H_5$, $R_1$ is $OC_2H_5$, $R_2$ is $OC_2H_5$ and $R_3$ is $OC_2H_5$.

11. A composition according to claim 8 in which R is $OCH_3$, $R_1$ is $OCH_3$, $R_2$ is $OC_2H_5$ and $R_3$ is $OC_2H_5$.

12. A composition according to claim 8 in which R is $OC_2H_5$, $R_1$ is $OC_2H_5$, $R_2$ is $C_2H_5$ and $R_3$ is $OC_2H_5$.

13. A composition according to claim 8 in which R is $C_2H_5$, $R_1$ is $OC_2H_5$, $R_2$ is $OC_2H_5$ and $R_3$ is $OC_2H_5$.

14. A composition according to claim 8 in which R is $OCH_3$, $R_1$ is $OCH_3$, $R_2$ is $C_2H_5$ and $R_3$ is $OC_2H_5$.

15. A compound having the general structural formula $$\begin{array}{c} R\diagdown \overset{S}{\underset{\diagup}{\uparrow}} \\ R_1 \end{array} PSCH_2\overset{CH_3}{\underset{|}{C}}=N \cdot NH\overset{O}{\underset{\|}{C}}CH_2SP \begin{array}{c} \diagup R_2 \\ \diagdown R_3 \end{array}$$

in which each of R and $R_2$ is an alkyl or alkoxy group and each of $R_1$ and $R_3$ is an alkoxy group.

16. A compound according to claim 15 in which R is $OC_2H_5$, $R_1$ is $OC_2H_5$, $R_2$ is $OC_2H_5$ and $R_3$ is $OC_2H_5$.

17. A compound according to claim 15 in which R is $C_2H_5$, $R_1$ is $OC_2H_5$, $R_2$ is $OC_2H_5$ and $R_3$ is $OC_2H_5$.

18. A compound according to claim 15 in which R is $OCH_3$, $R_1$ is $OCH_3$, $R_2$ is $OC_2H_5$ and $R_3$ is $OC_2H_5$.

19. A compound according to claim 15 in which R is $OC_2H_5$, $R_1$ is $OC_2H_5$, $R_2$ is $C_2H_5$ and $R_3$ is $OC_2H_5$.

20. A compound according to claim 15 in which R is $C_2H_5$, $R_1$ is $OC_2H_5$, $R_2$ is $C_2H_5$ and $R_3$ is $OC_2H_5$.

21. A compound according to claim 15 in which R is $OCH_3$, $R_1$ is $OCH_3$, $R_2$ is $C_2H_5$ and $R_3$ is $OC_2H_5$.

* * * * *